United States Patent [19]

Christian

[11] Patent Number: 5,380,338
[45] Date of Patent: Jan. 10, 1995

[54] LAPAROSCOPE HOLDER WITH ROTATABLE GRIPPING PADS

[75] Inventor: Steven C. Christian, New Brighton, Minn.

[73] Assignee: Minnesota Scientific, Inc., St. Paul, Minn.

[21] Appl. No.: 188,101

[22] Filed: Jan. 27, 1994

Related U.S. Application Data

[63] Continuation of Ser. No. 940,177, Sep. 3, 1992, abandoned.

[51] Int. Cl.6 .............................................. A61B 19/00
[52] U.S. Cl. .................................... 606/130; 606/205
[58] Field of Search ........................... 606/1, 106–108, 606/110, 113, 130, 142, 205–211; 128/749–751, 20; 81/487; 294/115

[56] References Cited

U.S. PATENT DOCUMENTS

| | | | |
|---|---|---|---|
| 840,380 | 1/1907 | Savidge | 294/115 |
| 2,355,631 | 8/1944 | Carter | 158/76 |
| 2,543,017 | 2/1951 | Hagan | 294/115 |
| 2,544,142 | 3/1951 | Dritley | 294/115 |
| 2,631,585 | 3/1953 | Siebrandt | 606/205 |
| 2,831,174 | 4/1958 | Hilmo | 606/206 |
| 3,506,012 | 4/1970 | Brown | 606/157 |
| 4,038,987 | 8/1977 | Komiya | 606/157 |
| 4,898,157 | 2/1990 | Messroghli et al. | 606/208 |
| 4,944,741 | 7/1990 | Hasson | 606/206 |
| 4,949,707 | 8/1990 | LeVahn et al. | 128/20 |
| 5,100,411 | 3/1992 | Koutrouvelis | 606/130 |
| 5,131,379 | 7/1992 | Sewell | 606/205 |
| 5,213,100 | 5/1993 | Summ | 606/130 |
| 5,224,680 | 7/1993 | Greenstein et al. | 128/20 |

FOREIGN PATENT DOCUMENTS

| | | | |
|---|---|---|---|
| 0653544 | 1/1986 | Switzerland | 606/206 |
| 0219742 | 6/1968 | U.S.S.R. | 606/130 |
| 9107922 | 6/1991 | WIPO | 606/130 |

OTHER PUBLICATIONS

Automated Medical Products Corp., *Laparoscopic Surgery With the Iron Intern ®-Your Most Dependable Assistant*, Date Unknown.

Surgical Products, *Laparoscopic Holder*, Apr. 1992; *Instrument Holder*, Apr. 1992.

Leonard Medical, Inc., *First Assistant* brochure and ordering information sheet, Apr. 1, 1992.

Thompson Surgical Instruments, Inc., undated letter, price list advertisements for Universal Laparoscopic Instrument Holder System.

*Primary Examiner*—Stephen C. Pellegrino
*Assistant Examiner*—Glenn K. Dawson
*Attorney, Agent, or Firm*—Kinney & Lange

[57] ABSTRACT

A device for clamping a medical instrument includes a pair of gripping arms that are movable between a closed and an open position. The gripping arms are pivotally movable with respect to each other and the device includes means for moving the gripping arms between the open and the closed position. In addition, the gripping arms are rotatably mounted to a support arm that is part of a support apparatus for holding the medical instrument.

6 Claims, 5 Drawing Sheets

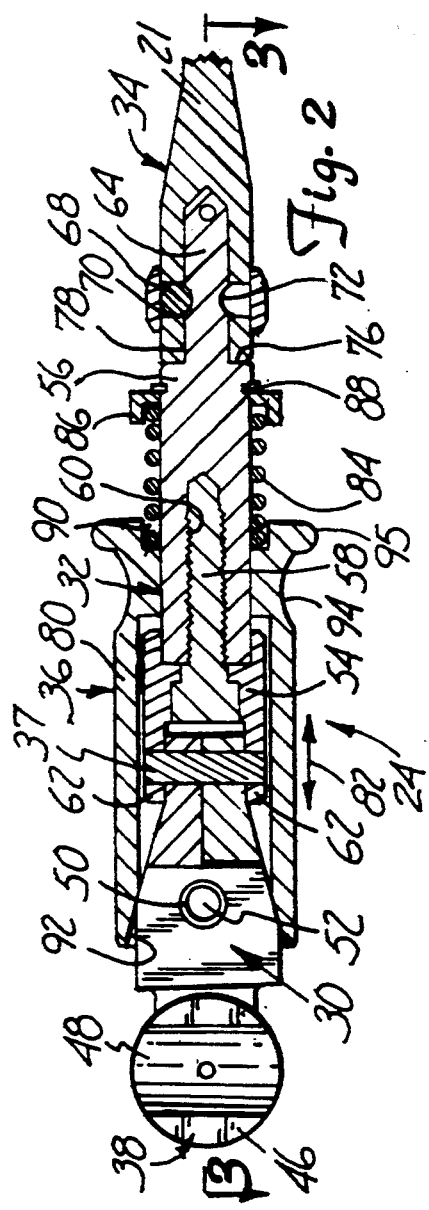
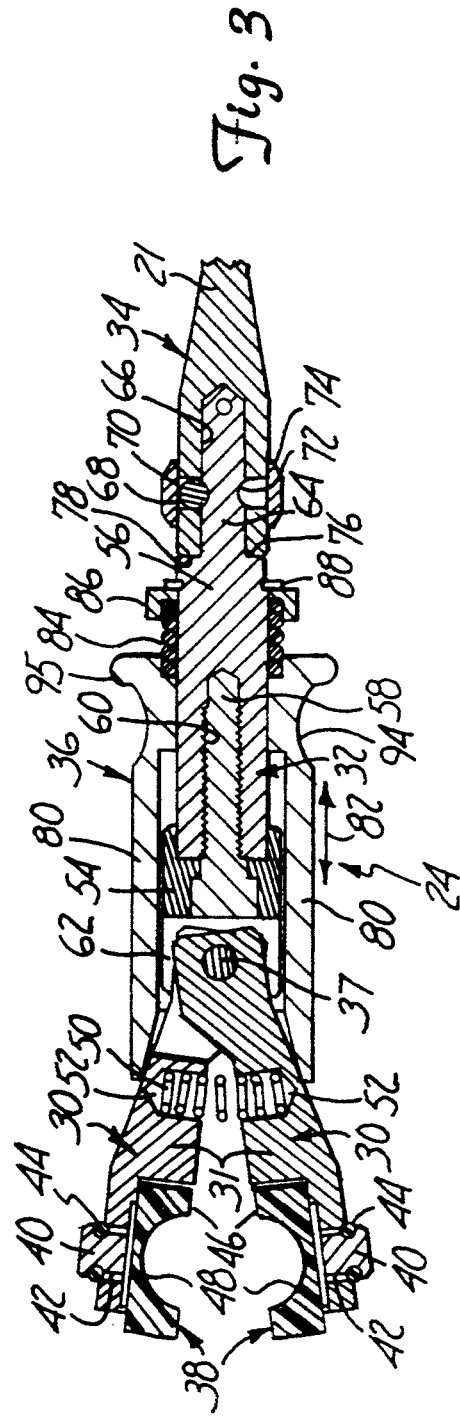

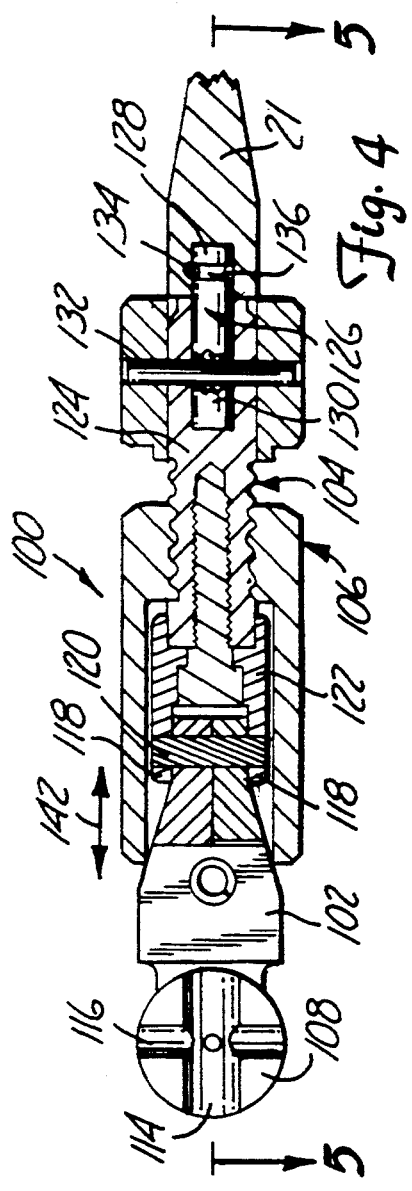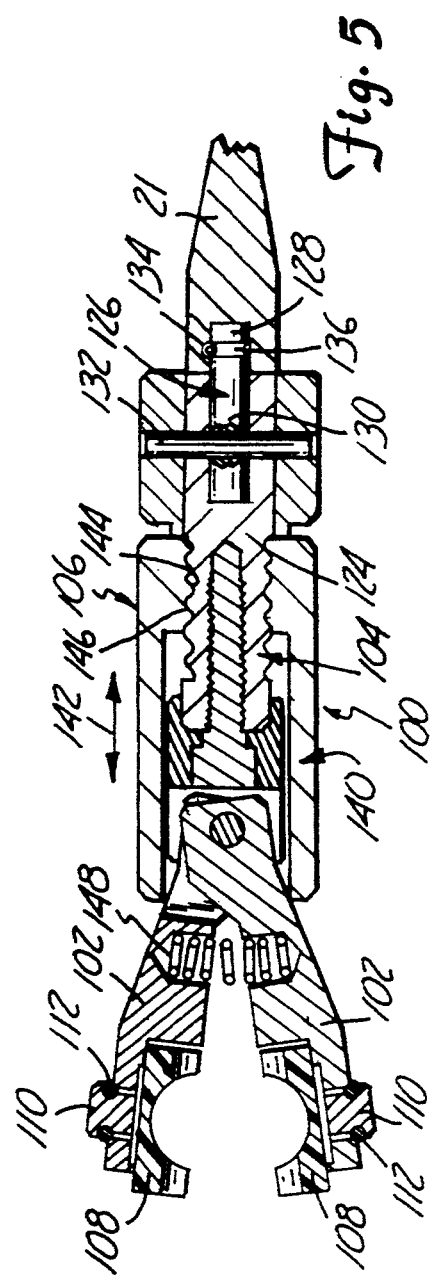

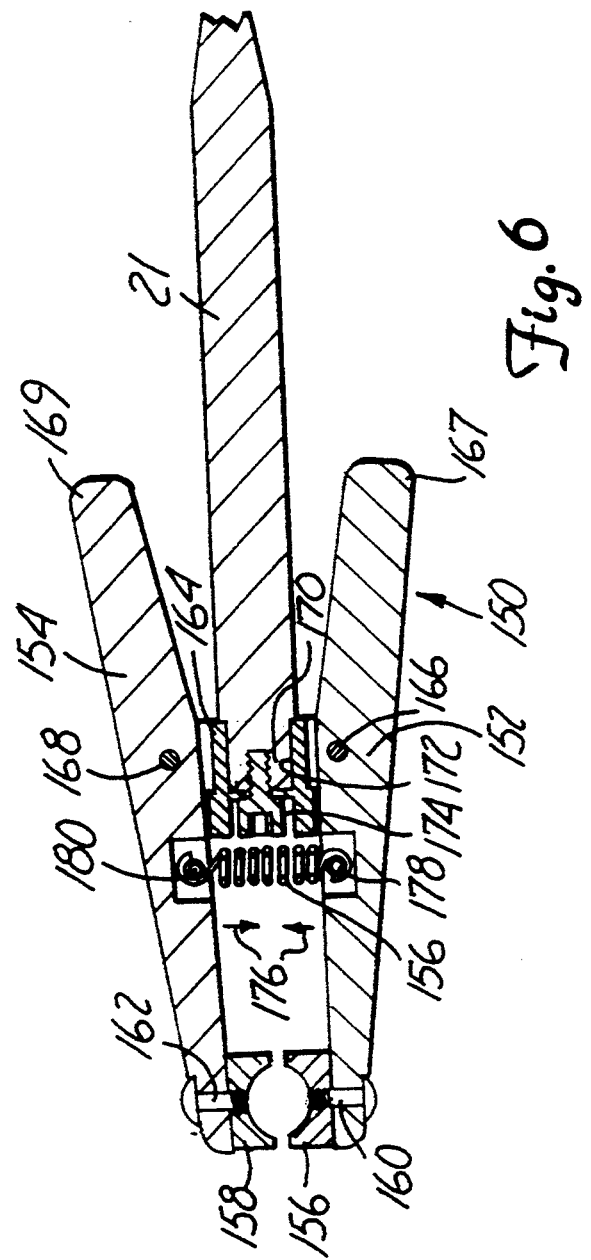

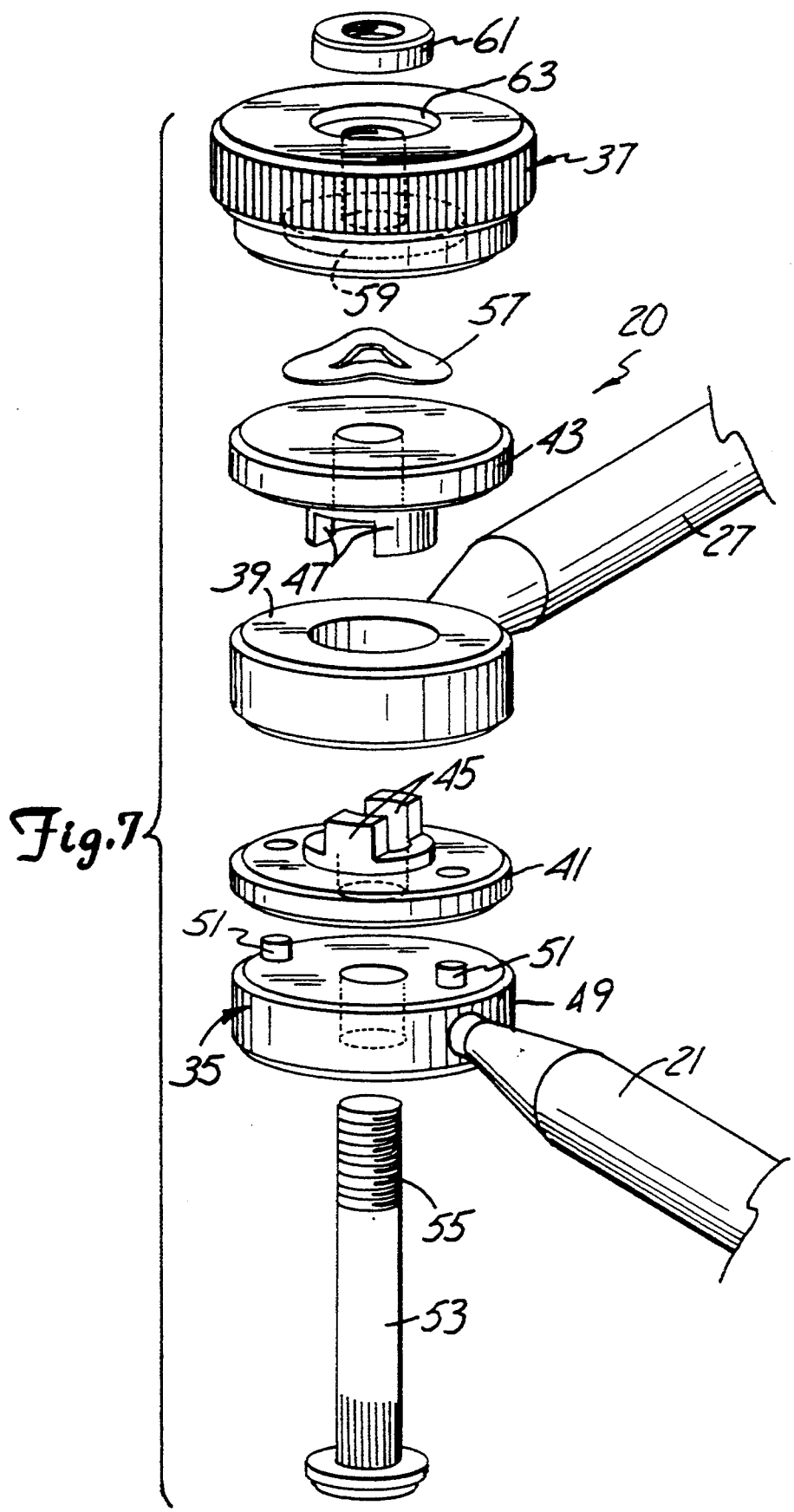

LAPAROSCOPE HOLDER WITH ROTATABLE GRIPPING PADS

This is a continuation of application Ser. No. 07/940,177, filed Sep. 3, 1992, now abandoned is claimed pursuant to 35 USC § 120.

BACKGROUND OF THE INVENTION

The present invention relates to a device for holding medical instruments. More particularly, the present invention relates to a laparoscope holder that permits quick release and multi-directional adjustment of a laparoscope.

The use of laparoscopes in abdominal and pelvic surgery is popular because laparoscopes allow the surgeon to perform complex minimally invasive surgical techniques while significantly reducing a patient's pain and discomfort resulting from large incisions made during common open surgery. The laparoscopic surgeon needs to have unobstructed mobility about the operating table during laparoscopic surgery procedures. However, the laparoscopic surgeon's mobility is hampered because the surgeon must interact with the surgical assistant(s), the camera assistant, the anesthesiologist, the scrub nurse, and the circulator.

Another critical aspect during laparoscopic surgery is stability and adjustment of the laparoscope. A steady, fixed visual field is crucial to the success of the highly precise procedures used during laparoscopic surgery such as intracorporeal suturing. Typically, a camera assistant holds the laparoscope. Besides occupying precious space around the operating table, the camera assistant may cause problems if the assistant fatigues or anticipates surgical movements during complex surgical operations. To overcome these difficulties and increase the stability of the laparoscope image, a variety of mechanical and robotic clamping systems have been developed.

These systems typically consist of a positionable arm that has a gripping device for holding the laparoscope. The positionable arms are designed to mimic the configuration and function of the human arm. For example, some arms have pivotally connected sections (Minnesota Scientific, Inc., St. Paul, Minn.), flexible sections (Flex Bar Machine Corp., Islandia, N.Y.), and pneumatically adjustable pivotally connected sections (Aesculap, Burlingame, Calif.).

The gripping device should permit quick release and allow multi-directional adjustment of the laparoscope. The prior art devices fail to adequately perform these tasks. For example, the gripping device of the Flex Bar laparoscope holder arm is a C-shaped clip into which the laparoscope is clamped. This device fails to provide adequate support for the laparoscope. The gripper device on the arm has a complicated two-piece construction that is difficult to work with. In addition, none of the other prior art gripping devices allows for quick release and multi-directional adjustment of the laparoscope.

SUMMARY OF THE INVENTION

A device for clamping a medical instrument includes a pair of gripping arms that are movable between a closed and an open position. The gripping arms are pivotally movable with respect to each other and the device includes means for moving the gripping arms between the open and the closed position. In addition, the gripping arms are rotatably mounted to a support arm that is part of a support apparatus for holding the medical instrument.

BRIEF DESCRIPTION OF THE DRAWINGS

FIG. 2 is a cross-sectional view of the holder illustrated in a closed position;

FIG. 3 is a cross-sectional view of the holder taken along the line 3—3 in FIG. 2 illustrated in an open position;

FIG. 4 is a cross-sectional view of a second embodiment of the holder illustrated in a closed position;

FIG. 5 is a cross-sectional view of the second embodiment of the holder taken along the line 5—5 in FIG. 4 illustrated in an open position;

FIG. 6 is a cross-sectional view of the third embodiment of the holder illustrated in a closed position; and FIG. 7 is an exploded perspective view of a clamp of the present invention.

DETAILED DESCRIPTION OF THE PREFERRED EMBODIMENTS

Figure 1:
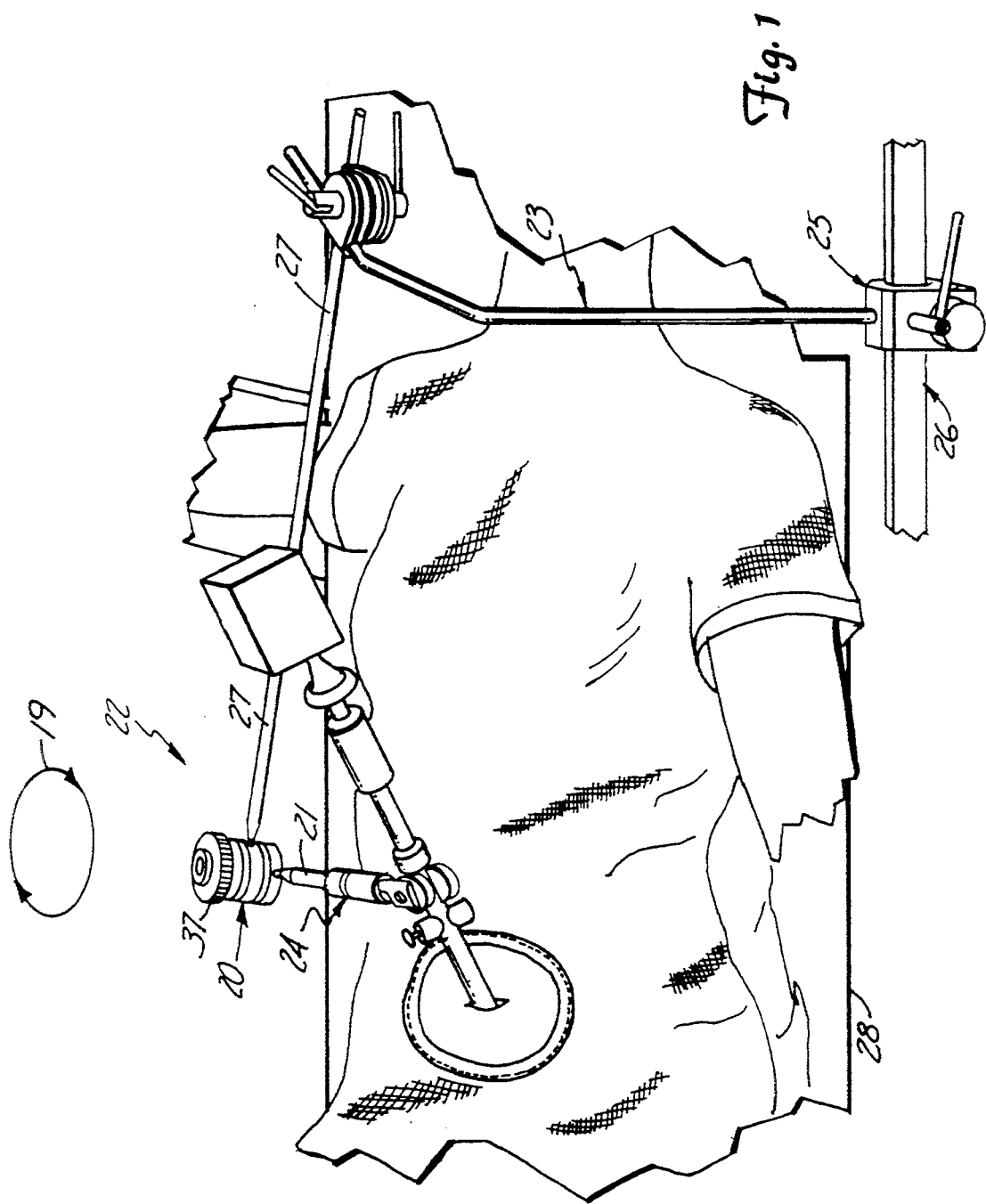
FIG. 1 is a perspective view of the holder of the present invention when it is attached for use in an operating room.

The laparoscope holder of the present invention is generally illustrated at 24 in FIG. 1. Although the term laparoscope holder is used, it will be understood that the holder of the present invention can be used to hold other types of medical instruments other than laparoscopes such as endoscopes and forceps. The laparoscope holder 24 is attached to an arm assembly 22. The arm assembly 22 is supported by a retractor support apparatus 23 that is used to support the laparoscope holder over an operating table 28. The operating table 28 includes side rails 26 (one only being shown) to which the retractor support assembly 23 is attached by a clamp 25. A suitable clamping device is described in U.S. Pat. No. 2,355,631.

The arm assembly 22 includes a clamp 20, a first arm section 21, and a second arm section 27. The clamping device 20 permits the laparoscope holder 24 to be pivoted as indicated by arrows 19 about a pivotal axis running through the clamping device 20.

The device 20, as best illustrated in FIG. 7, includes a bottom bolt section 35, a top knurl knob 37, and a middle swivel ring 39. The device 20 also includes friction pads 41 and 43. Each friction pad has a pair of interlocking prongs 45 and 47, respectively that interlock. Although preferably a pair of prongs is shown for each friction pad, other arrangements and numbers of friction prongs are includable within the scope of the present invention. The friction pads 41 and 43 are preferably made from an autoclavable material such as Victrex PEEK, a poly(aryletherketone) manufactured by ICI of the United Kingdom.

The bottom section 35 includes the friction pad 41 secured to a bottom ring 49 by a pair of connecting pins 51 and a bolt 53 extending through and fixedly attached to the ring 49. The bolt 53 extends axially through the middle swivel ring 39 and both friction pads 43 and 41. The bolt 53 has a threaded end portion 55 that threadably engages the knurled knob 37. A curved washer spring 57 is positioned about the bolt 53 in a spring cavity 59 in the knurl knob 37. A retaining ring 61 is swedged on to the end of the bolt section next to the threaded end portion 55 and is adapted to be received by a retainer cavity 63 within the knurled knob 37.

The arm section 27 is attached to the middle swivel ring 39 while the arm section 21 is attached to the bottom ring 49. To secure the arm section 21 at a selected angle with respect to the arm section 27, the knurled knob is turned clockwise, which will work against the bias of the spring 59 and bring the friction pads 41 and 43 together against swivel ring 39 in frictional engagement. To release the clamp 20 from frictional engagement so that the arm sections 21 and 27 can be moved with respect to each other, the knurled knob is turned counterclockwise. It will be appreciated that the retainer 61 prevents disengagement of the knurled knob from the bolt section.

The laparoscope holder 24 includes a pair of gripping arms 30, as best illustrated in FIGS. 2 and 3. The gripping arms 30 are pivotally mounted on to a rotatable main body member 32. The rotatable main body member 32 is rotatably connected to a connecting end portion 34 of the first arm section 21. A mechanism for pivoting 36 pivots the gripping arms between an open and closed position about a pivot pin 37.

Each of the gripping arms includes a gripping pad 38 rotatably mounted on the gripping arm main body 31. The gripping pad 38 is preferably made from stainless steel. However, the pad may be constructed from other flexible, strong, lightweight, and autoclavable materials such as Victrex PEEK, a poly(aryletherketone) manufactured by ICI of the United Kingdom. The pad 38 includes a shaft portion 40 extending therefrom and through an aperture 42 located within the gripping arm main body 31. The pad 38 is rotatably held on to the gripping arm main body 31 by an O-ring 44 circumferentially engaging a groove in the shaft 40. The O-ring 44, when disposed about the shaft 40, is larger in diameter than the aperture 42 thereby retaining the pad 38 on to the gripping arm 30. The O-ring 44 permits rotation of the pad while providing frictional force so that the pad can be selectively rotated and retained at a selected angular position. A retaining ring (not shown) can also be attached to the shaft to prevent the pad from falling off the arm if the O-ring should break.

The gripping pad 38 is preferably cylindrical in configuration and has an inwardly facing surface 46 having an arcuate groove 48. When the gripping pads are brought towards each other, the arcuate grooves form a generally cylindrical gripping surface that conforms generally to the cylindrical surfaces of a laparoscope or other instrument to be held. The gripping pads 38 may also have a second arcuate groove (not shown) that is preferably oriented transversely to the arcuate groove 48. The second arcuate groove is preferably of a different size than the arcuate groove 48 to accommodate instruments having a different diameter size.

The gripping arms 30 are biased from each other by a coil spring 50. The coil spring 50 is preferably disposed at each end in oppositely facing bores 52 located in the respective gripping arm main body 31.

The main body 32 includes a forward member 54 for pivotally retaining the gripping arms 30 and a rearward member 56, which engages the connecting end portion 34 of the arm section 21. The forward member 54 preferably includes a rearwardly extending threaded shaft portion 58 that threadably engages a threaded bore 60 of the rearward member 56. The forward member 54 includes forwardly extending spaced apart side walls 62 that are disposed on opposing sides of the gripping arms 30. The side walls 62 in cooperation with the pivot pin 37 pivotally retain the gripping arms.

The rearward member 56 also includes a rearwardly extending shaft portion 64 that engages a bore 66 within the connecting end portion 34. Ball bearings 68 are disposed within apertures 70 that are positioned circumferentially within the connecting end portion 34. The rearward shaft portion 64 includes an annular groove 72 that is adapted to receive inwardly extending portions of the ball bearings 68. An annular ring 74 extends circumferentially about the connecting portion 34 and retains the ball bearings within the apertures 70 and in contact with the annular groove 72. The rearward member 56 also includes a shoulder 76 that abuts against a distal end surface 78 of the connecting portion 34. The shoulder 76 by abutting against the distal end surface 78 while permitting the ball bearings 68 to engage the groove 72 attaches the laparoscope holder 24 to the arm section 21 while permitting free rotation of the laparoscope holder with respect to the arm section 21.

The mechanism for pivoting 36 includes a cylindrical sleeve 80 disposed around the main body 32 and movable in the general direction indicated by arrows 82. The sleeve 80 is biased in a forward position by a coil spring 84 disposed about the rearward member 56 of the main body 32. A spring retainer 86 is attached to the rearward member 56 and provides a back stop to the spring 84. Preferably, the spring retainer is held in place by the rearward bias of the spring 84 and a retaining ring 88 engaging an annular groove in the member 56 on a side of the ring 88 opposite from the spring 84. A forward or distal portion of the spring 84 is disposed within an annular groove 90 of the sleeve 80.

The sleeve 80 includes an inwardly facing tapered surface 92 for engaging angled surfaces of the gripping arms 30, as best illustrated in FIG. 2. An annular finger groove 94 and annular flange 95 are disposed on an outer surface of a rearward portion of the sleeve 80 provide a mechanism for gripping the sleeve 80 and moving the sleeve rearwardly as illustrated in FIG. 3. Moving the sleeve 80 rearwardly removes a forward portion of the sleeve from a forward position surrounding the gripping arms 30 thereby permitting the coil spring 50 to bias the gripping arms from each other to an open position and release the instrument held within the pads 38. Releasing the sleeve permits the coil spring 84 to bias the sleeve 80 forwardly and encompass the arms 30, bringing the arms together to a closed position. The spring 84 provides enough force to bias the sleeve in the forward position while permitting movement of the sleeve rearwardly using only hand pressure. It will be appreciated that although the arcuate grooves 48 are of a selected diameter, instruments having a diameter larger than the diameter of the grooves are held by the pads due to the spring type force supplied by the coil spring 84.

The laparoscope holder 24, as described above, provides a surgeon with several degrees of freedom. First, the holder may be freely rotated about its own longitudinal axis. Second, the pads 38 are also rotatable so that instruments can be positioned at various angles with respect to the longitudinal axis of the holder 24. Third, the clamp 20 permits angular movement of the holder. Lastly, the instrument can be released quickly or engaged quickly by simply moving the sleeve 80 rearwardly or by permitting the sleeve to be biased forwardly by the spring 84.

A second embodiment of the present invention is illustrated in FIGS. 4 and 5. Similar to the embodiment of FIGS. 2 and 3, the embodiment 100 of the laparoscope holder of the present invention includes gripping arms 102 that are pivotally attached to a main body 104, which in turn is rotatably connected to the first arm section 21. A mechanism for pivoting 106 pivots the gripping arms 102 between an open position and a closed position.

The gripping arms 102 also include gripping pads 108. Each pad 108 is rotatably attached to the respective gripping arm 102 by a shaft 110 that extends through a bore within the respective arm 102 and is rotatably secured by an O-ring 112 as previously described with respect to the embodiment illustrated in FIGS. 2 and 3. The pad 108, as illustrated in FIG. 4, includes an arcuate groove 114 of a first size and an arcuate groove 116 of a second smaller size. Since the pad is rotatable, the grooves can be positioned to accommodate instruments of different sizes.

The arms 102 are attached in a manner similar to the embodiment illustrated in FIGS. 2 and 3 to the main body 104. The main body 104 is similar to the main body 32 by preferably having a forward member 122 and a rearward member 124 that are attached to each other. The forward member 122 includes spaced apart side walls 118 and a pivot pin 120 that extends through each arm 102 and the side walls 118 to pivotally secure the arms 102 to the forward member 122. The rearward member 124 is secured to the first arm section 21 through a connecting pin 126 rotatably secured at a first end portion 128 to the first arm section 21 and secured to the rearward member at a second end portion 130 by a dowel pin 132. The dowel pin 132 extends through the member 124 and through the pin 130 thereby securing the connecting pin 130 to the member 124. The end portion 128 is rotatably secured to the first arm section 21 by a pin 134 extending through the arm section 21 and engaging an annular groove 136 within the connecting pin 126 thereby permitting rotation of the connecting pin 130 and the holder 100 with respect to the first arm section 21 while securing the holder to the arm section 21.

The mechanism for pivoting 106 includes a sleeve 140 that is movable along the general direction indicated by arrows 142. The sleeve 140 includes a threaded bore 144 threadably engaging a threaded surface 146 of the rearward member 124. The sleeve 140 is moved to a forward position as illustrated in FIG. 4 and to a rearward position as illustrated in FIG. 5 by rotating the sleeve. When the sleeve is in the forward position, the sleeve encompasses the arms 102, bringing the arms together to a closed or gripping position. When the sleeve is moved to a rearward position as illustrated in FIG. 5, the sleeve is moved from engagement with the arms 102 thereby permitting a coil spring 148 to bias the arms 102 to an open position.

It will be appreciated that the embodiment 100 illustrated in FIGS. 4 and 5 has the same degrees of freedom as the embodiment illustrated in FIGS. 2 and 3.

A third embodiment 150 of the present invention is illustrated in FIG. 6. The embodiment 150 includes first and second gripping arms 152 and 154 that are biased to a closed position by a coil spring 156. The gripping arms 152 and 154 include gripping pads 156 and 158, that are each rotatably secured to the respective gripping arms by screws 160 and 162, respectively.

The gripping arms 152 and 154 are each pivotally attached to a connecting block 164 by pins 166 and 168, respectively and include arm portions 167 and 169 that are disposed on a side of the respective pivot pin opposite from the gripping pad. The block 164 is rotatably secured to the first arm section 21 by an end portion 170 of the first arm section 21 rotatably engaging a bore 172 within the connecting block 164. A screw 174 inserted through a hole within the connecting block 164 threadably engages the end portion 170 to secure the block 164 to the first arm section 21.

The spring 156 biases the arms 152 and 154 inwardly, that is towards each other, as generally indicated by arrows 176. Preferably, the coil spring 156 is secured to the respective arm by engaging a pin 178 and 180, respectively.

It will be appreciated that the same degrees of freedom are enjoyed by embodiment 150 as the embodiments described in FIGS. 2 and 3, and FIGS. 4 and 5. The holder 150 is rotatable about the axis of the first arm section 21. The pads 156 and 158 are rotatable to change the angle of the instrument being held. Lastly, the gripping arms are easily moved between a closed and an open position for engaging and releasing an instrument.

Although the present invention has been described with reference to preferred embodiments, workers skilled in the art will recognize that changes may be made in form and detail without departing from the spirit and scope of the invention.

What is claimed is:

1. A gripping device for holding a medical instrument from a support apparatus having a support arm, the device comprising:

gripping arms for gripping an instrument, the gripping arms being pivotally mounted together and being adapted for rotatably mounting to a support arm, the gripping arms being pivotal between an open position and a closed position;

means for moving the gripping arms between the open and closed position to release and grip an instrument, the means for moving the gripping arms comprising a sleeve operably engaging an exterior surface of the gripping arms, the sleeve being movable between a gripping arm engaging position and a gripping arm release position wherein when the sleeve is in the gripping arm engaging portion, the gripping arms are in the closed position and wherein when the sleeve is in the gripping arm release position, the gripping arms are in the open position; and a gripping pad rotatably attached to each gripping arm wherein each gripping pad has an arcuate groove formed therein for engaging the instrument.

2. The device of claim 1 and further including a biasing means for biasing the gripping arms to the open position.

3. The device of claim 1 further including a biasing means for providing a biasing force for biasing the sleeve to the gripping arm engaging position while permitting movement of the sleeve against the biasing force to the gripping arm release position.

4. The device of claim 1 wherein the gripping arms are pivotally connected to a main body, and wherein the main body has an outer threaded surface and the sleeve has inwardly facing threads in cooperation with the threads of the main body such that when the sleeve is turned, the sleeve is movable between the gripping arm engaging position and the gripping arm release position.

5. The device of claim 1 and further including a biasing means for biasing the gripping arms to the closed position.

6. The device of claim 5 and further including a rotatable member, which has a first portion and a second portion that rotate with respect to each other, the first portion is mounted to the gripping arms and the second portion is adapted to be mountable to the support arm so that the gripping arms can rotate with respect to the support arm.

* * * * *